US008900183B2

(12) United States Patent
Widdecke

(10) Patent No.: US 8,900,183 B2
(45) Date of Patent: Dec. 2, 2014

(54) MEDICAL DEVICE AND GUIDE DEVICE THEREFOR

(71) Applicant: Biotronik SE & Co. KG, Berlin (DE)

(72) Inventor: Heinrich Widdecke, Beelitz (DE)

(73) Assignee: Biotronik SE & Co. KG, Berlin (DE)

( * ) Notice: Subject to any disclaimer, the term of this patent is extended or adjusted under 35 U.S.C. 154(b) by 113 days.

(21) Appl. No.: 13/626,318

(22) Filed: Sep. 25, 2012

(65) Prior Publication Data

US 2013/0085444 A1 Apr. 4, 2013

Related U.S. Application Data

(60) Provisional application No. 61/542,824, filed on Oct. 4, 2011.

(51) Int. Cl.
*A61M 31/00* (2006.01)
*A61M 25/00* (2006.01)

(52) U.S. Cl.
CPC ......... *A61M 25/0012* (2013.01); *A61M 25/005* (2013.01)
USPC ....................................... 604/95.04; 606/129

(58) Field of Classification Search
CPC ............. A61M 2025/0046; A61M 2025/0047; A61M 25/005; A61M 2025/0062; A61M 25/0012
USPC .............................. 604/95.04, 95.01; 606/129
See application file for complete search history.

(56) References Cited

U.S. PATENT DOCUMENTS

| 5,603,697 A | * | 2/1997 | Grundy et al. | 604/95.04 |
| 5,902,290 A | * | 5/1999 | Peacock et al. | 604/526 |
| 7,160,297 B2 | * | 1/2007 | Nesbitt | 606/45 |
| 2004/0186377 A1 | | 9/2004 | Zhong et al. | |
| 2004/0230271 A1 | | 11/2004 | Wang et al. | |
| 2006/0173422 A1 | * | 8/2006 | Reydel et al. | 604/271 |

FOREIGN PATENT DOCUMENTS

WO 2007000148 1/2007

OTHER PUBLICATIONS

European Search Report and Notes to the European Search Report on European Patent Application No. EP 12 18 3870, dated Feb. 8, 2013 (4 pages).

* cited by examiner

*Primary Examiner* — Theodore Stigell
(74) *Attorney, Agent, or Firm* — Buchanan Ingersoll & Rooney PC

(57) ABSTRACT

A guide device including a polymer and/or plastic tube, in particular a tube containing a polysiloxane, through the continuous opening of which a cable which is moveable in the continuous opening has been routed. To markedly reduce the wear caused by the cable rubbing in the continuous opening of the tube, a coating is provided on the outer surface of the cable and/or the inner surface of the continuous opening, which includes mainly particles that are substantially spherical and/or cylindrical and can move freely at least on the particular surface (e.g., outer surface of the cable and/or inner surface of the continuous opening). Furthermore, a medical device containing such a guide device, and a method for manufacturing the guide device or the medical device are described.

9 Claims, 4 Drawing Sheets

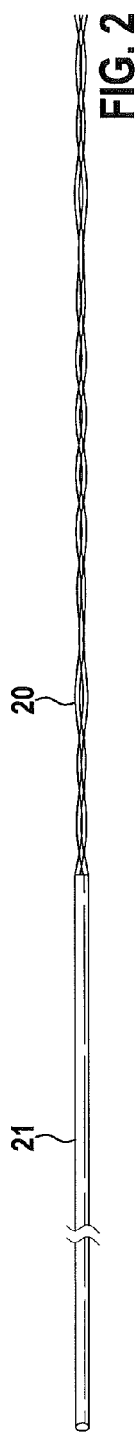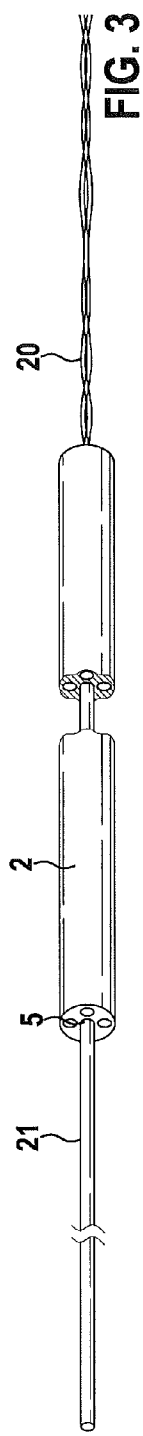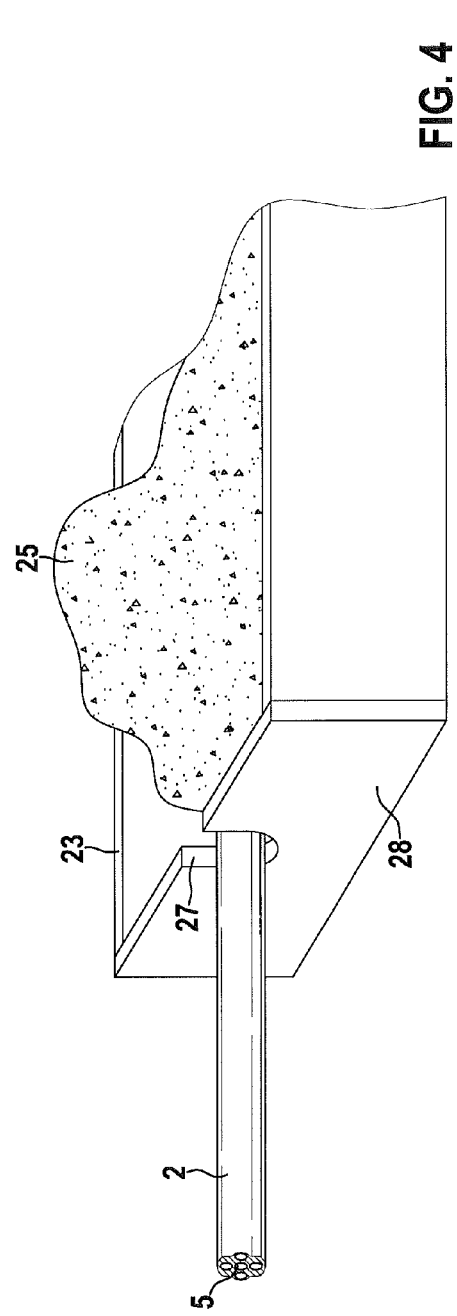

MEDICAL DEVICE AND GUIDE DEVICE THEREFOR

CROSS-REFERENCE TO RELATED APPLICATIONS

This patent application claims the benefit of U.S. Provisional Patent Application No. 61/542,824, filed on Oct. 4, 2011, which is hereby incorporated by reference in its entirety.

TECHNICAL FIELD

The present application relates to a guide device comprising a polymer and/or plastic tube and, in particular, a tube containing a polysiloxane, through the continuous opening of which a cable or strip which is moveable in the opening has been routed. The present application furthermore relates to a medical device and, in particular, a catheter comprising such a guide device, and a method for manufacturing such a guide device or such a medical device.

BACKGROUND

A medical device in the sense of the present application includes elongated catheters or electrode leads which can be inserted into a living body temporarily or permanently. Electrode leads are permanent implants which remain in, for example, the heart, brain, or spinal cord and are used to exchange therapeutic or diagnostic signals between an electromedical implant (e.g., implantable cardiac pacemaker, defibrillators, neurostimulators, cochlear implants, etc.) and an electrode surface at the opposite end of the electrode lead. A catheter is a small rigid or flexible tube that can be introduced into a body cavity to be treated. Such tubes are offered in various diameters. The body cavities, such as, for example, the bladder, stomach, intestine, vessels, etc., as well as the ear and heart, are probed, evacuated, filled, or rinsed with a catheter. This is done for diagnostic and/or therapeutic reasons.

All medical devices in the sense of the present application typically have the same or similar design. They have a proximal end and a distal end which points in the direction of the treatment site. Mounted on this distal end are devices relevant to therapy or diagnostics, such as, for example, electrodes for stimulating organs of the body or sensing body signals. The proximal end serves as an interface to an implant or external control, and therapy or diagnostic devices, and can also serve to enable control by a physician, such as, for example, controlling the flexible distal end using a control device. Situated between the proximal end and distal end of the medical device is an elongated body comprising at least one flexible or rigid tube. Such a tube is typically comprised of a continuous opening, which is also referred to as a lumen, and extends along the longitudinal axis of the tube. If the body is comprised of a plurality of tubes which extend in parallel and form a single unit, it is comprised of a plurality of lumina and is therefore referred to as a multi-lumina tube. Each of the lumina, in particular the outer lumina which are offset in the radial direction from the longitudinal axis, can form the continuous opening of the tube of a guide device.

Guide devices are generally used to guide cables or strips. The cables or strips in the guide devices can be used, in particular, to enable the distal end to be controlled, and/or to transmit therapeutic or diagnostic signals.

The catheters referred to as medical devices, in particular so-called ablation catheters which are used primarily in electrophysiology for the thermal destruction of a conduction path in the heart, typically comprise an aforementioned multi-lumina tube as catheter body, in the case of which several or all outer lumina can serve as lumina of a guide device. This means that a cable—in this case a control cable or control band—is guided in one lumen or each of the lumina. Each control cable extends through one of the lumina. Defined pulling motions on the cables are employed to redirect the catheter tip away from the longitudinal axis and thereby guide the catheter tip to the desired tissue region to be treated. For control, the physician typically uses a handle to operate the control cables or strips, which causes the cable to move relative to the lumen. Various electrode surfaces are located on the catheter tip, which are used to direct radio frequency signals into the tissue region for ablation.

A relative motion between a cable and lumen takes place even with electrode leads that remain in the body permanently; such electrode leads are also encompassed by the term "catheter" in the sense of the present application.

The body thereof, which is also referred to as an electrode body, basically has the same structure as the above-described catheter body and is generally equivalent thereto. In contrast, however, the electrode lead remains in the body permanently and is therefore exposed to other stresses. Likewise, such an electrode lead comprises control cables in the rarest cases, as well as electrically conductive supply cables or strips for transmitting electrical signals from the electromedical implant—on the proximal end of the electrode lead—to an electrode on the distal end of the electrode lead, or vice versa. These electrical supply cables likewise extend in the lumen of a tube. The electrode body can likewise be formed of a plurality of tubes in an interconnection, wherein the stranded conductors extend in one or more of the tubular lumina. The electrode lead is subjected to a continuous flexural load by, for example, the heart, which is in permanent motion, thereby resulting in relative motion between each tube in an electrode body and the stranded conductor.

In the following, the system comprised of a flexible tube (or rigid tube) having a continuous opening (lumen) and a cable extending therein (control cable or supply cable of an electrode lead) is referred to as the guide device. This means that, in a body of a medical device as an interconnection of a plurality of tubes, every tube in which a cable is routed is a guide device. The guide device forms the core of the medical device. This medical device can include even more devices for various applications, such as, for example, a balloon, connectors for measuring devices, a syringe for providing a fluid for treatment (e.g., a drug or another pharmaceutically active substance) or diagnosis (e.g., with contrast medium), or the like. Another lumen which temporarily accommodates a guide wire can also be present.

The guide device according to the subject of the present application can also be used in medical devices other than those stated, e.g., in minimally invasive instruments. In these devices, control is likewise performed using guide or puller cable(s) which move relative to a flexible tube or rigid tube.

In such a guide device, in which relative motion takes place between two different materials (usually, but not limited to, a polymer and/or plastic material on the side of the tube, and a metallic material on the side of the cable), a great deal of wear is typically observed. It is possible for a cable to become worn through by the surrounding tube material. In the control of catheters, in contrast, increased frictional force is observed, which encumbers control and makes therapy difficult or more time-consuming than expected.

A problem addressed by the present application is therefore that of creating a guide device or a medical device having greatly reduced wear or friction. A further problem is that of providing a simple and cost-effective method for manufacturing such a guide device or such a medical device.

The present application is directed toward overcoming one or more of the above-identified problems.

SUMMARY

The above-stated problem(s) is solved by a guide device which has a coating on the outer surface of the cable and/or the inner surface of the continuous opening, which is comprised mainly of particles which are substantially spherical or cylindrical and can move freely at least on the particular surface.

According to the subject matter of the present application, fine-grained particles are therefore disposed between the tube and the cable, which form a rolling coating or a rollable layer due to their spherical or cylindrical shape and their capability to move freely on the particular surface. The kinetic friction which, according to the prior art, is present between the materials and has resulted in the large amount of wear or the sluggishness, is therefore prevented and replaced by rolling friction. The wear and sluggishness are hereby reduced to a very considerable extent, thereby greatly extending the service life of the medical device comprising the guide device, or simplifying the use thereof. Flexibility is likewise greatly increased.

Therefore, an essential feature of the stated coating is that the particles, which can move on the surface of the cable or the tube, enhance the relative motion between the cable and the tube, and prevent stiction. The particles are not distributed on the surface of the cable or the surface of the tube in a homogeneous manner, but rather irregularly, and do not form a layer that completely covers the particular surface, since the particles should be allowed to move freely on the particular surface. Preferably, the particles can move freely not only on the particular surface but also in three-dimensional space. As such, they can roll on the cable surface and on the inner surface of the tube.

Within the scope of the present application, the expression "substantially spherical or cylindrical" with regard to the particles means that they have an approximately spherical or cylindrical shape. They need not be in the shape of ideal spheres, cylinders or particles; deviations from this shape are possible and are encompassed by the present application. The shape of the particles must ensure that the particles can roll on the surface of the cable and/or the inner surface of the tube when relative motion occurs between the cable and the tube. A slight deviation from the ideal spherical or cylindrical shape is therefore insignificant for the property of rolling.

In one embodiment of the present application, the particles of the lining cannot be crushed and/or cannot degrade, and can also be biocompatible. These properties of the particles are desirable, in particular, if the guide device will be employed in the body for a very long time so that the rolling property of the particles does not worsen over the course of the service life, which would increase wear.

The particles of the coating are preferably made of one of the following materials: corundum, silica sand, polyamide, polyimide, and/or Teflon. It is also possible to mix different particles made of one or more of the stated materials.

It is further preferable for the particles to have a mean diameter that is greater than or equal to 20 μm. It is furthermore preferable for this mean diameter to be greater than or equal to 20 μm and not greater than 60 μm; and particularly preferably that the particles have a mean diameter of approximately 50 μm. To determine the mean of the diameter, a microscopic image of the particles is taken and, therein, the diameter of at least 10 particles is measured, the arithmetic mean of which yields the mean diameter of the particles. The stated dimensions of the particles are advantageous since, if finer materials were used, a rolling effect would no longer be possible, and larger particles would not be free to move.

In a preferred embodiment, the tube of the guide device is comprised of a central lumen and at least one outer lumen, wherein one or more of the outer lumina preferably accommodate the cable or cables. The material of the tube is preferably silicone material, however, other materials are contemplated. The multi-lumina tube can also include further outer layers, wherein the layer structure of the tube serves to attain properties that are favorable for the application, such as, for example, good anti-frictional properties and sterilizability due to an appropriate outer layer, and favorable mechanical properties (e.g., elasticity, a small bending radius, good bending properties, etc.).

The above-stated problem is furthermore solved by a medical device, in particular, a catheter or an implantable electrode lead which includes a guide device having the above-described coating. The medical device has the advantages indicated in conjunction with the guide device according to the subject matter of the application.

A further exemplary solution to the above-noted statement of the problem is the simple method for manufacturing a guide device, which can be implemented cost-effectively, in which the plastic and/or polymer tube is provided, and a dosing plunger which is comprised of a wire mesh, for instance, is then moved through an accumulation of particles which are substantially spherical or cylindrical and can move independently of one another, and then through the continuous opening of the plastic and/or polymer tube.

The dosing plunger is preferably pulled through the opening in the plastic and/or polymer tube using, for example, a puller cable, and the spherical or cylindrical particles that were taken up during the passage through the accumulation of particles are transferred to the inner side of the tube. It is furthermore advantageous if, after the first time the particles have been brought into the continuous opening of the tube, the dosing plunger is moved through the continuous opening one more time in order to better distribute the particles in the opening.

After the spherical or cylindrical particles are applied to the inner surface of the continuous opening of the tube, the cable is inserted into the opening, thereby creating the guide device.

The above-stated problem(s) is also solved by a method for producing a medical device, in particular a catheter, in which first the guide device is manufactured using the above-described method, and the further elements of the medical device are then placed on the guide device, being connected thereto, for example. As a further step, after the manufacture of the guide devices, a plurality of these guide devices can be preferably combined after their manufacture to form an interconnection, to thereby create a multi-lumina tube. Preferably, furthermore, more tubes can be added to the interconnection in addition to the guide wires, so that a continuous opening for a temporarily present guide wire is available, for example.

Further aspects, objects, features, advantages, and possible applications will become apparent from the following description of embodiments and the figures. All of the described and/or graphically depicted features form the subject matter of the present invention, either alone or in any combination, even independently of their wording in the claims or their dependency references.

DESCRIPTION OF THE DRAWINGS

The drawings show, schematically:

FIG. 2 shows a view of a dosing plunger including a puller cable, from the side, FIG. 3 shows a tube of a guide device including dosing a plunger and a guide cable, in a perspective view from the side, FIG. 4 shows the tube of the guide device according to FIG. 3 when placing the particles which are located in a container, in a perspective view from the side.

DETAILED DESCRIPTION

Figure 1:
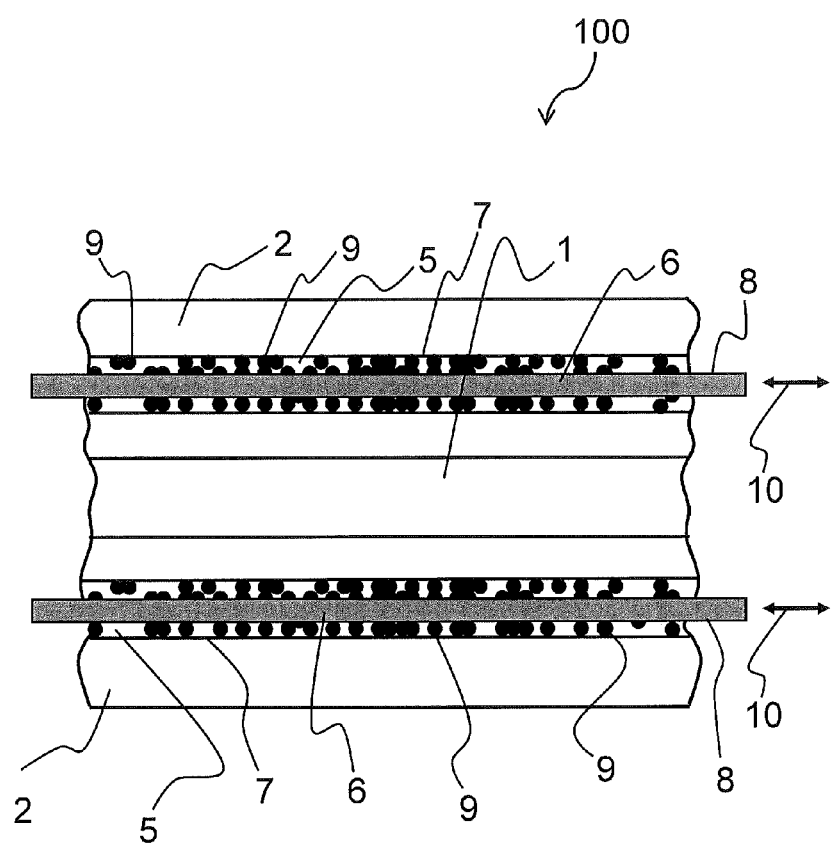
FIG. 1 shoes a longitudinal section through a section of a guide device according to the subject matter of the present invention.
Figure 5:
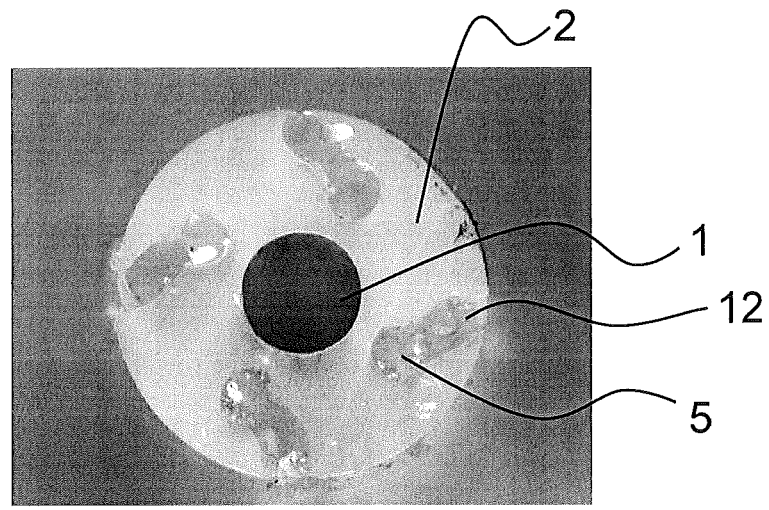
FIG. 5 shows a cross section of a guide device after a wear test on a first comparative example.
Figure 6:
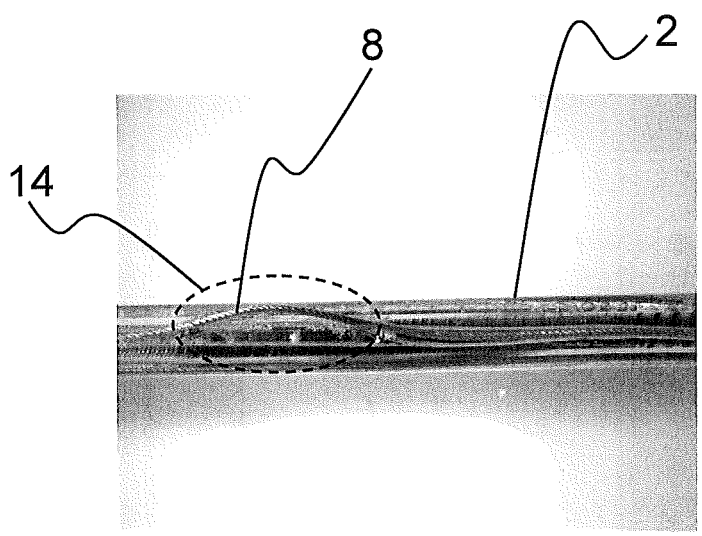
FIG. 6 shows the worn guide device of the first comparative example in a view from the side.

FIG. 1 shows the longitudinal section of a medical device 100 comprising two guide devices of the subject matter of the present application. The device 100 is comprised of a multi-lumina tube having an inner tube 1 and at least one outer tube 2 which is offset in the radial direction relative to the central lumen, each of which has an outer lumen 5 in the form of a continuous opening. The inner tube 1 and the at least one outer tube 2 are joined to form an interconnection (multi-lumina tube). The multi-lumina tube—i.e., tubes 1 and 2—is comprised of a polymer and/or plastic tube which preferably contains polysiloxane.

Cables 6 are disposed in outer lumina 5. Cable 6 is made of, for example, 7×7 twisted single wires with a Teflon-type casing. The longitudinal section shown in FIG. 1 shows only two of these outer lumina 5, however, more are contemplated.

It is understood that, as an alternative, the device 100 can also comprise only one continuous opening with a cable, or any other number of continuous openings. Alternatively, a continuous opening can also extend through the inner tube 1.

Situated between the inner surface 7 of outer tube 2, which forms continuous opening 5, and the outer surface 8 of cable 6 is a row of substantially spherical or cylindrical particles 9 comprised of corundum, silica sand, polyamide, polyimide, and/or Teflon, and having a mean diameter of greater than or equal to 20 μm, preferably not greater than 60 μm, and particularly preferably having a mean diameter of approximately 50 μm.

Due to particles 9, when a relative motion occurs between cable 6 and outer tube 2 in the longitudinal direction (as indicated by double arrow 10), the stiction that would normally exist between the inner surface 7 of outer tube 2 and the outer surface 8 of cable 6 is replaced by rolling friction which greatly reduces wear. The rolling friction occurs between inner surface 7 and particles 9, and between particles 9 and surface 8 of cable 6. As a result, cable 6 no longer rubs into the silicone material, nor through it.

In a configuration shown in FIG. 1, a special wear test was carried out on a test specimen that has the design according to the subject matter of the present application, and compared with the results of the same wear test carried out on two test specimens which did not embody the solution according to the present invention. The test specimens had a length of approximately 60 mm. The results are presented in FIGS. 5-8.

In the wear test, a certain type of rotational motion of the test specimen is induced to generate a relative motion between the cables and the outer lumen. The motion is intended to simulate a medical device that has been permanently implanted in a beating heart.

In a first test, the test specimen had moved a multi-lumina tube, in which each of the four outer lumina 5 thereof accommodated a cable 8 formed of 7×7 twisted single wires with a Teflon-type casing, through 2.5 million cycles at 7,500 revolutions per minute. Neither the outer lumen 5 nor the cable had been provided on the surface thereof with the coating (rolling layer) according to the subject matter of the present application. After the end of the stress test, the wear in the tube 2 was inspected. It was found that one cable 8 had worn through the outer tube 2 (see region 14 in FIG. 6), and the other three cables 8 had clearly worn into the silicone material. The resulting expansions 12 of continuous openings 5 are clearly visible in the cross-section shown in FIG. 5.

Figure 7:
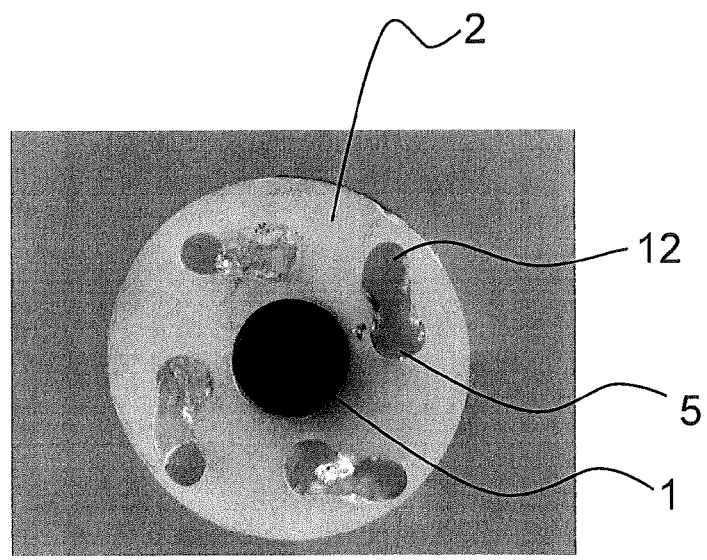
FIG. 7 shows a cross-section of a guide device after a wear test on a second comparative example.
Figure 8:
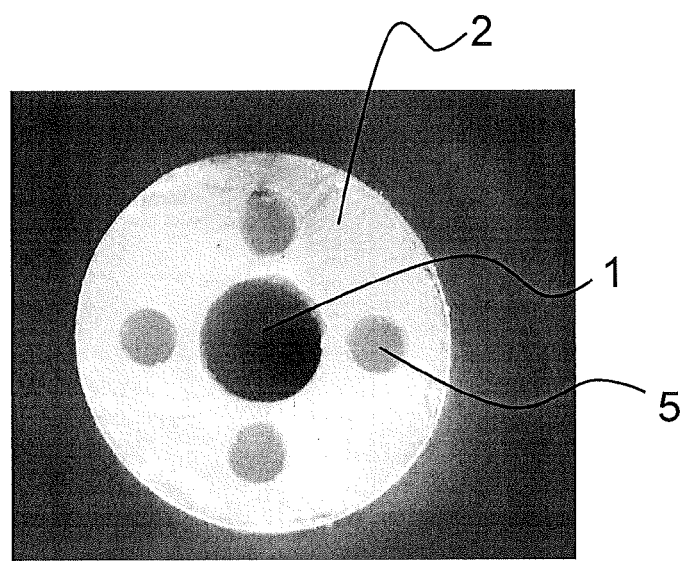
FIG. 8 shows a cross-section of a guide device according to the subject matter of the present application, after a wear test.

Distinct wear was found in a second test after the same stress was applied, even when a configuration was used that was otherwise identical to that used in the first test, and with an additional coating applied to the inner surface of the tube, which was comprised of high-strength, two-component silicone material, referred to as MED-6670 from the company NuSil. FIG. 7 shows a cross section of such a test specimen after completion of the stress test. In this case as well, the cables 6 have worn almost entirely through the tubular wall. Expansions 12 of openings 5, which were created by the wear, are also clearly visible.

In a third test, a guide device according to the subject matter of the present application was carried out in the same configuration as in the first test with four continuous openings and cables situated therein, between which a coating comprised substantially of spherical or cylindrical particles made of polyamide particles had been provided. After a run time of 100 million cycles at 7,500 revolutions per minute, i.e., a 40-fold longer stress period, only minor wear was found, as indicated in the cross section-shown in FIG. 8, in which continuous openings 5 show only minor deviations from the ideally round shape.

The manufacture of a guide device according to the subject matter of the present application will now be described with reference to FIGS. 2-4. The manufacture is described with reference to a single tube, as an example. In principle, this manufacturing process is also suitable for medical devices, such as, for example, catheter bodies or electrode bodies which include a multi-lumina tube having guide devices as stated in FIG. 1.

FIG. 2 shows a dosing plunger 20 which is connected to a puller cable 21. Dosing plunger 20 is a plunger that can take up the particles in dry form or together with a fluid and distribute them across a long path within opening 5 of tube 2 of the guide device. Dosing plunger 20 is comprised of a wire helix, for instance, which includes at least two elongated, wound wires or a mesh of such wires. The quantity of particles to be conveyed is regulated, inter alia, by the length of dosing plunger 20. For longer tubes, the frequency of the procedure of pulling through can be repeated as necessary. Puller cable 21 is longer than continuous opening of outer lumen 5 to be provided with particles.

Dosing plunger 20 is connected to puller cable 21 which serves as force transmitter and handling means when dosing plunger 20 is pulled through opening 5 of tube 2 of the guide device.

First, puller cable 21 is pulled through continuous opening 5 to be provided with particles, as shown in FIG. 3. Puller cable 21 is pulled through opening 5 until dosing plunger 20 rests against an end of outer lumen 5. This is the right end of the silicone tube, in the example shown in FIG. 3.

In this position, the silicone tube is inserted into slot 27 in a front wall 28 of a container (supply box) 23 containing an accumulation 25 of spherical or cylindrical particles to be moved into the continuous opening. The silicone tube is fixedly clamped by slot 27. To this end, slot 27 has a slightly smaller inner diameter as compared to the outer diameter of the silicone tube. Dosing plunger 20 is embedded in the accumulation 25 of particles, and so dosing plunger 20 is completely surrounded by the particles. By pulling on puller cable 21, which is not depicted in FIG. 4, dosing plunger 20 is now pulled through continuous opening 5. The particles picked up from accumulation 25 are distributed by dosing plunger 20 on the inner surface 7 of the continuous opening 5.

The silicone tube is now removed from slot 27 of container 23. Dosing plunger 20 is then pulled through continuous opening 5 once more to distribute the particles that had been moved into continuous opening 5 across the entire inner surface of continuous opening 5.

The method described above for placing particles onto the inner surface 7 of continuous opening 5 is then repeated, as necessary, for the further continuous openings of tube 2. The puller cable or strip is then inserted into the continuous opening(s) of outer lumen 5, thereby completing the manufacture of the guide device.

To finalize the medical device, the guide device is then connected to the further elements of the medical device.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE CHARACTERS

1 Inner tube
2 Outer tube
5 Continuous opening in the form of outer lumen
6 Cable
7 Inner surface of outer lumen 5
8 Outer surface (jacket surface) of guide cable 6
9 Particle
10 Double arrow
12 Expansion of opening 5 in the outer lumen caused by wear
14 Marked region
20 Dosing plunger
21 Guide cable
23 Container
25 Accumulation of cylindrical or spherical particles in container 23
27 Slot
28 Side wall
100 Medical device

I claim:

1. A guide device comprising:
   a polymer and/or plastic tube comprised of a polysiloxane and including a continuous opening;
   a cable inserted into the continuous opening and which is moveable in the continuous opening; and
   a coating provided on an outer surface of the cable and/or an inner surface of the continuous opening, wherein the coating is comprised mainly of particles that are substantially spherical or cylindrical and can move freely at least on a particular surface of the cable or continuous opening.

2. The guide device according to claim 1, wherein the particles of the coating cannot be crushed and/or degraded.

3. The guide device according to claim 1, wherein the particles have a mean diameter that is greater than or equal to 20 μm.

4. The guide device according to claim 1, wherein the particles have a mean diameter that is greater than or equal to 20 μm and not greater than 60 μm.

5. The guide device according to claim 1, wherein the particles have a mean diameter that is approximately 50 μm.

6. The guide device according to claim 1, wherein the particles are made of corundum, silica sand, polyamide, polyimide, Tetrafluoroethylene and/or Polytetrafluoroethylene.

7. The guide device according to claim 1, wherein the particles form a rolling coating wherein the particles roll on at least the particular surface of the cable or continuous opening when relative motion occurs between the cable and the tube.

8. The guide device according to claim 1, wherein the particles are irregularly spaced on the outer surface of the cable and/or the inner surface of the continuous opening such that they do not completely cover the particular surface of the cable or continuous opening.

9. A medical device comprising a catheter or implantable electrode lead, comprising a guide device according to claim 1.

* * * * *